(12) United States Patent
Southard et al.

(10) Patent No.: US 7,678,870 B2
(45) Date of Patent: Mar. 16, 2010

(54) PROCESSABLE MOLECULARLY IMPRINTED POLYMERS

(75) Inventors: Glen E. Southard, Park City, UT (US); George M. Murray, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/599,062

(22) PCT Filed: Oct. 4, 2004

(86) PCT No.: PCT/US2004/032575

§ 371 (c)(1), (2), (4) Date: Sep. 19, 2006

(87) PCT Pub. No.: WO2005/103655

PCT Pub. Date: Nov. 3, 2005

(65) Prior Publication Data

US 2007/0197746 A1    Aug. 23, 2007

Related U.S. Application Data

(60) Provisional application No. 60/560,668, filed on Apr. 8, 2004.

(51) Int. Cl.
*C08F 4/52*   (2006.01)
*G01N 21/76*   (2006.01)
*C07F 5/00*   (2006.01)
*C08F 2/38*   (2006.01)

(52) U.S. Cl. .................. 526/172; 526/240; 526/274; 526/279; 526/320; 526/336; 525/245; 436/164; 436/166; 436/172; 534/16

(58) Field of Classification Search ............... 436/164, 436/166, 172; 534/16; 526/172, 240, 274, 526/279, 320, 336; 525/245
See application file for complete search history.

(56) References Cited

U.S. PATENT DOCUMENTS

| | | | |
|---|---|---|---|
| 5,587,273 A | 12/1996 | Yan et al. | |
| 5,639,615 A | 6/1997 | Selvin et al. | |
| 6,642,318 B1 | 11/2003 | Chiefari et al. | |
| 6,699,717 B1 | 3/2004 | Rao et al. | |
| 6,749,811 B2 | 6/2004 | Murray | |

*Primary Examiner*—Fred M Teskin
(74) *Attorney, Agent, or Firm*—Francis A. Cooch

(57) ABSTRACT

A process is provided herein for preparing molecularly imprinted polymers for detecting a target analyte by Reversible Addition Fragmentation Chain Transfer (RAFT). The process includes providing a complex having the formula $L_3M$ wherein L is a β-diketone ligand containing a chain transfer moiety and $L_3$ can be the same or different ligands, and M is a lanthanide element; reacting the complex with the target analyte to provide an adduct containing the target analyte; co-polymerizing the adduct with a monomer and cross-linking agent to provide a polymer; and removing the target analyte from the polymer to provide the molecularly imprinted polymer.

45 Claims, 2 Drawing Sheets

PROCESSABLE MOLECULARLY IMPRINTED POLYMERS

CROSS REFERENCE TO RELATED APPLICATIONS

The present application claims priority to U.S. provisional application Ser. No. 60/560,668 filed Apr. 8, 2004, the contents of which are incorporated by reference herein.

STATEMENT OF GOVERNMENTAL INTEREST

This invention was made with Government support under Contract No. F08650-03-C-D012 awarded by the U.S. Air Force. The Government has certain rights in the invention.

BACKGROUND OF THE INVENTION

1. Field of the Invention

The present invention relates generally to molecularly imprinted polymers comprising chelated lanthanides and a process for preparing them.

2. Background of the Art

A number of organophosphorus compounds are used as pesticides and nerve agents. For example, organophosphorus based pesticides, including paraoxon, parathion and diazinon are widely used in the agriculture industry and the resultant environmental pollution is well documented. Because of their toxicity and relatively high solubility in water, organophosphorus based pesticides pose a clear threat to drinking water and aquatic life. It is therefore necessary to monitor the levels of these materials in industrial waste water, agricultural runoff, and other environments to determine compliance with federal and state regulations and other safety guidelines, as well as efficiency of wastewater treatments.

In addition, organophosphorus based nerve gases, including tabun and the organo-fluorophosphorus compounds sarin and soman, are of particular concern as chemical weapons which can be used on battlefields or by terrorists in civilian populated areas. Concerns over the use of these chemicals, as well as leakages from aging stockpiles prompt the development of easily used portable devices which can provide real time monitoring capabilities for such compounds.

Chemical sensors must fulfill two goals: (1) the development of a specific chemical recognition element that allows a molecule, or class of molecule, to be identified, and (2) a means of signal transduction in which the presence of the molecule causes a measurable change in a physical property of the material. Although these goals are not always separable, the successful design of chemical sensors requires that both be satisfied.

Most transduction approaches are based on optical, resistive, surface acoustic wave, or capacitive measurements. These well-developed methods dominate largely because of their ease of operation, sensitivity, and cost. The chemical recognition elements in these detectors, however, lag far behind. Indeed, most reports on chemical sensors suggest that many other devices could be fabricated if only suitable chemical recognition units were available. The missing element is a general approach to chemical recognition that allows the rational design and assembly of materials in a stable and reusable form. The present invention solves this problem based on the fabrication of molecularly imprinted polymers (MIPs).

An MIP is generally described as a plastic cast or mold of the molecule of interest, where recognition is based on shape, much like a lock and key. MIPs are made by adding the molecule of interest to a solution of binding molecules that can be chemically incorporated into a polymer. See FIG. 1. These binders usually have an affinity for the target and form a complex.

The interactions that hold these complexes together include $\pi$-$\pi$ interactions, hydrogen bonding, metal-ligand binding, and even covalent bond formation, but they must be reversible. The binder must also have a chemical functionality that allows it to be irreversibly bound to polymers. Vinyl groups are a common functional group used to prepare many polymers, e.g., polyethylene, polystyrene, polyvinylalcohol, and polyvinylchloride. The target-binder complex is dissolved in excess matrix monomer (for example, styrene) and possibly other additives such as a cross-linker and porogens (solvents).

In a typical sensor fabrication, a solid plastic mass, consisting of the matrix and binder, is obtained which is chemically bound to the polymer/cross-linker matrix and the target molecule. Removal of the target is possible since it is reversibly bound to the binder. The cavity it leaves behind is permanently shaped like the target.

Sensors for organophosphorus compounds can be based on the luminescence of a lanthanide ion. See, for example, U.S. Pat. No. 6,749,811 B2, which is herein incorporated by reference. The process is enhanced when the lanthanide has sensitizing ligands. If the ligands can be polymerized a MIP sensor can be made. However, the best sensitizing ligands, such as $\beta$-diketones, may lose their ability to complex a lanthanide when a vinyl substitutent is added. Accordingly, what is needed is some other means for polymerization for making MIPs suitable for sensors.

SUMMARY OF THE INVENTION

In accordance with one embodiment of the present invention, a process is provided for preparing a molecularly imprinted polymer for detecting a target analyte. The process comprises the steps of (a) providing a complex comprising a compound of the general formula $L_3M$ wherein L is the same or different and is a $\beta$-diketone ligand containing the same or different chain transfer moiety and M is a lanthanide element; (b) reacting the complex with a target analyte to provide an adduct containing the target analyte; (c) co-polymerizing the adduct with a monomer and cross-linking agent under effective polymerization conditions to provide a polymer; and, (d) removing the target analyte from the polymer to provide the molecularly imprinted polymer.

In accordance with a second embodiment of the present invention, a polymer is provided comprising the reaction product of (a) a complex comprising a compound of the general formula $L_3M$ wherein L is the same or different and is a $\beta$-diketone ligand containing the same or different chain transfer moiety and M is a lanthanide element, the complex being capable of binding an analyte to be detected; (b) a monomer; and (c) optional crosslinking agent, wherein said polymer undergoes a detectable luminescence change upon exposure to the analyte to be detected.

In accordance with a third embodiment of the present invention, a molecularly imprinted polymer is provided, the molecularly imprinted polymer being obtained by the steps of (a) providing a reaction product of (i) a complex comprising a compound of the general formula $L_3M$ wherein L is the same or different and is a $\beta$-diketone ligand containing the same or different chain transfer moiety and M is a lanthanide element and (ii) a target analyte; (b) copolymerizing the reaction product of step (a) with monomer and optional crosslinking agent under effective polymerization conditions to form a polymer; and (c) removing the target analyte from the polymer to provide a molecularly imprinted polymer which selectively binds to the target analyte and undergoes a detectable luminescence change when the target analyte binds thereto.

BRIEF DESCRIPTION OF THE DRAWINGS

Various embodiments are described below with reference to the drawings wherein.

DETAILED DESCRIPTION OF PREFERRED EMBODIMENT(S)

Figure 1:
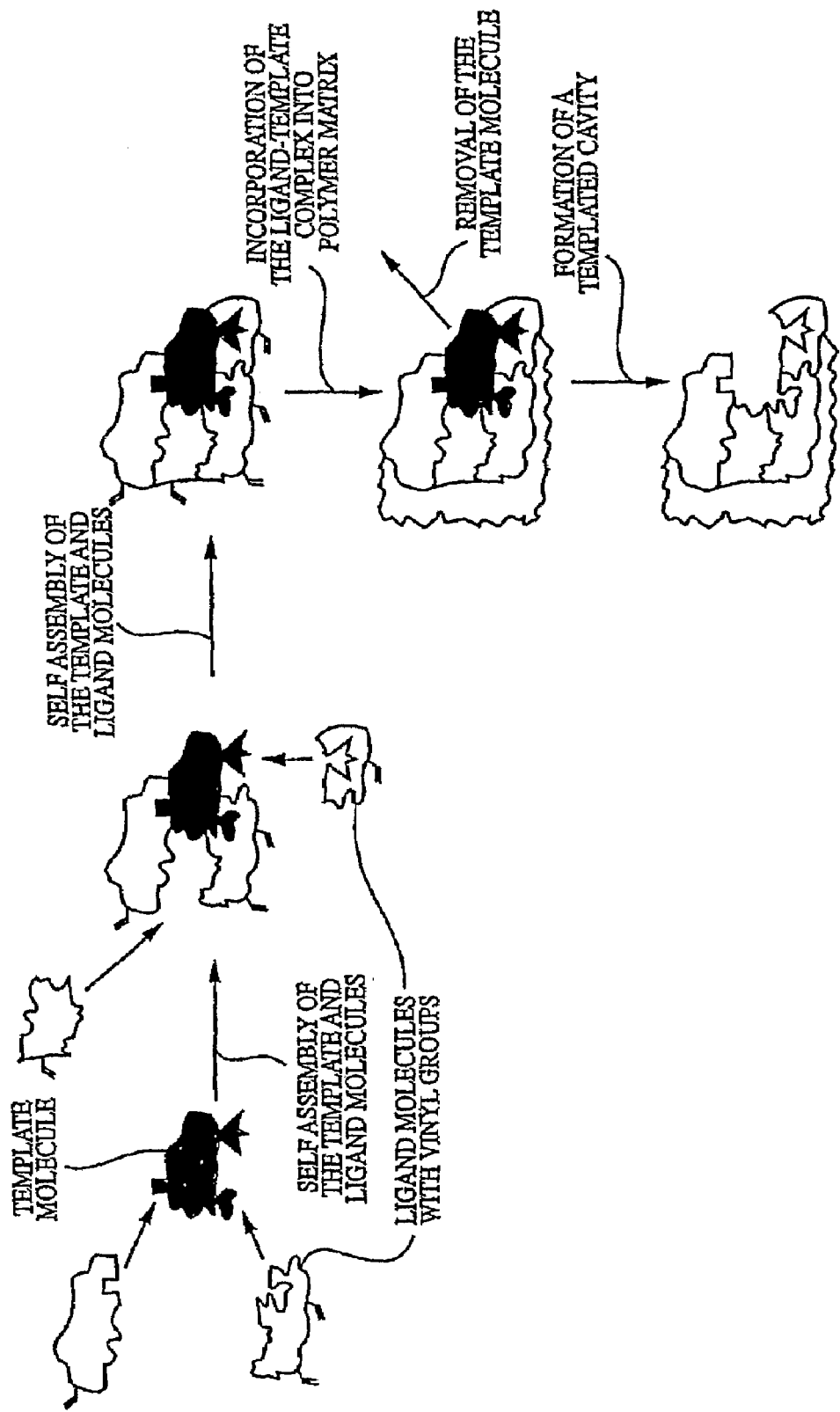
FIG. 1 is a schematic flow chart illustrating a known method of molecular imprinting to obtain a molecularly imprinted polymer; and, FIG. 2 is a schematic flow chart illustrating the synthesis procedures described in Examples 1 to 5.

The present invention relates to a process for preparing a molecularly imprinted polymer for sensitized lanthanide luminescence, thereby providing multiple criteria for selectivity for a target analyte, e.g., an organophosphorus compound, and virtually eliminating the possibility for false positive readings. The lanthanide elements, also known as the rare earth elements, consist of the elements having atomic numbers from 57 to 71. As used herein, the term "lanthanide" refers to the following elements of the periodic table: lanthanum (La), cerium (Ce), praseodymium (Pr), neodymium (Nd), promethium (Pm), samarium (Sm), europium (Eu), gadolinium (Gd), terbium (Th), dysprosium (Dy), holmium (Ho), erbium (Er), thulium (Tm), ytterbium (Yb), and lutetium (Lu). In the present invention, a lanthanide is chosen as the transducer because the trivalent lanthanide ions have excellent spectroscopic properties such as long luminescence lifetimes and narrow bandwidths, usually only a few nanometers. Preferred lanthanide ions that exhibit a narrow-line luminescence include the +3 ions of samarium, europium, dysprosium, terbium, and neodymium, with europium being most preferred.

As used herein, the terms "molecularly imprinted molecule", "molecularly imprinted polymer" and "MIP" refer to a molecular mold-like structure that has preorganized interactive moieties complementing the spacing of binding sites on a template or template molecule. The interactive moieties can be, for example, chemical groups of affinity ligands. The geometrical organization of interactive moieties imparts selective binding characteristics for the template substance onto the imprinted polymer. The term "selective binding interactions" is intended to refer to preferential and reversible binding exhibited by an imprinted polymer for its template molecule (e.g., organophosphorus compound) compared to other non-template molecules. Selective binding includes both affinity and specificity of the imprinted polymer for its template molecule.

The origins of molecularly imprinted molecules trace back to the notion of Linus Pauling that the body assembled a new protein complement (i.e., an antibody) by using the foreign intruder as a template. Although it was later determined that this is not how antibodies are selected in vivo, this template concept stimulated significant thought and research. Molecular imprinting creates specific recognition sites in materials, such as polymeric organic materials. Known molecular imprinting techniques involve crosslinking materials in the presence of a functional monomer or mixture of monomers. The template molecule interacts with a complementary portion of a functional monomer, either covalently or by other interactions such as ionic, hydrophobic or hydrogen bonding, so that recognition sites for the template molecule can be provided in the substrate material. The template molecule is then removed from the substrate to leave a "cavity" or recognition site. Pauling reasoned that shape specificity was obtained by using a target antigen to arrange the complementary shape of an antibody. Thus, a nonspecific molecule can be shaped to the contours of a specific target, and when the target is removed, the shape is maintained to give the antibody a propensity to rebind the antigen. This process is known as "molecular imprinting" or "templating."

The target or template molecule directs the positioning of the encapsulating antibody by the interactions that occur between certain sites on the target and complementary sites on the antibody. The sites that allow complementary associations are certain arrangements of atoms that exhibit an electrostatic attraction of a specific kind. These localized atomic arrangements are sometimes referred to as "functional groups." The functional groups on a molecule help to define the molecule's overall chemical properties. In general, the MIP should exhibit as closely as possible the reverse topology of the template molecule. For example, if the template molecule has a cationic group at a specific location, then the MIP should have an anionic group at that location.

The synthetic production of polymers with selective binding for a specific cation is achieved by providing polymers with cavities lined with complexing groups or "ligands" arranged to match the charge, coordination number, coordination geometry, and size of the target cation. Anion complexing polymers are made in a similar manner, but typically employ a trapped metal ion that has a large affinity for the anion in question. These cavity-containing polymers are produced by using a specific ion as a template around which monomeric complexing ligands will be self-assembled and later polymerized. The complexing ligands are ones containing functional groups known to form stable complexes with the specific ion and less stable complexes with other ions.

When lanthanide ions are chelated with appropriate ligands, a significant enhancement of the luminescence intensity is obtained. The chelated lanthanide complexes of the present invention provide a sensitive means of analysis with low limits of detection when incorporated in a MIP. For example, lanthanide ions can form complexes with various organic molecules such as $\beta$-diketones, polyaminopolycarboxylic acids (EDTA and the like), (poly)pyridines and calixarenes. Moreover, ligands containing organic chromophores possessing suitable photophysical properties provide highly luminescent lanthanide complexes. See, e.g., Jenkins, A., et al., "Ultratrace Determination of Selected Lanthamides by Luminescence Enhancement," *Anal. Chem.*, 68(17):2974-2980 (1996) (the entire disclosure of which is incorporated herein by reference). With a careful selection of complexing ligands, metal complexes can be synthesized by mixing stoichiometric amounts of a lanthanide metal salt and the complexing ligand(s) in an aqueous solution and evaporating to near dryness. Water or alcohol/water mixtures of the lanthanide metal and ligand in stoichiometric ratios, evaporated to dryness, are preferred to obtain near quantitative yield of the desired complex compound. In one embodiment, to make complexes that contain target anions, mixed ligand complexes that have a one-to-one stoichiometric ratio of target anion to complex can be employed. This can be accomplished by synthesizing lanthanide metal ion complexes with the proper coordination number of tightly binding ligands such that a single target analyte could bind by replacing a very weakly bound substitutent.

The present invention is directed to a MIP obtained from a polymerization process referred to as Reversible Addition Fragmentation Chain Transfer ("RAFT"). RAFT is a controlled free radical polymerization and insures the formation of high polymer with a narrow molecular weight distribution. The process involves a chain transfer agent such as, for example, a dithioester agent. The process allows the use of a broad spectrum of monomers and a highly controlled topology and morphology. Since it does not involve conjugation to a β-diketone aromatic ring, it does not interfere with the ligand complexing ability. Accordingly, the RAFT process advantageously prepares lanthanide-containing RAFT MIPs for the detection of target molecules such as organophosphorus compounds. The detection limits are in the low parts per billion range by luminesce spectroscopy and are free from interference from phosphorus compounds not used as the imprinting species. Particularly desirable are the RAFT star polymers described herein for providing fast kinetics, high solubility and processability.

In general, RAFT polymerization is described in U.S. Pat. Nos. 6,747,111, 6,737,488, 6,642,318 and 6,458,968, and in foreign publication WO 98/01478, all of which are incorporated by reference herein.

The RAFT star polymerization process for preparing a MIP of the present invention comprises the steps:

(a) providing a complex comprising a compound of the general formula $L_3M$ wherein L is the same or different and is a β-diketone ligand containing the same or different chain transfer moiety and M is a lanthanide element;

(b) reacting the complex of step (a) with a target analyte to provide an adduct containing the target analyte;

(c) co-polymerizing the adduct of step (b) with a monomer and optional cross-linking agent under effective polymerization conditions to provide a polymer; and (d) removing the target analyte from the polymer to provide the MIP.

These steps are described in more detail hereinbelow.

Providing the Lanthanide Complex

The preferred lanthanide for use herein is trivalent europium ($Eu^{+3}$) and the MIP of the present invention will be exemplified with europium although other lanthanides as described hereinabove can alternatively be employed.

The ligand L is a β-diketone generally having the structure:

$$R^1—C(O)—CR^2_2—C(O)—R^3$$

wherein $R^1$ is a hydrocarbon group having 1 to about 20 carbons and containing a chain transfer moiety; $R^2$ can be the same or different and is hydrogen or a hydrocarbon group having from 1 to about 12 carbon atoms and $R^3$ is a straight or branched chain alkyl group of 1 to about 12 carbon atoms optionally containing one or more halogen atoms.

In one embodiment, the hydrocarbon group of $R^1$ is a substituted or unsubstituted alkyl group; a cycloalkyl group; a substituted or unsubstituted aryl group, e.g., a phenyl group, a naphthyl group and the like; a substituted or unsubstituted alkaryl group, e.g., 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylphenyl group (mesityl group) and the like; a substituted or unsubstituted aralkyl group, e.g., phenylmethyl group (benzyl group), phenylethyl group (phenethyl group), triphenylmethyl group (trityl group) and the like; a substituted or unsubstituted monocyclic aromatic group, e.g., benzene, methylbenzene (toluene), 1,2-dimethylbenzene (o-xylene), 1,3-dimethylbenzene (m-xylene), 1,4-dimethylbenzene (p-xylene), 1,3,5-trimethylbenzene (mesitylene), 1,2,3-trimethylbenzene, 1,2,4-trimethylbenzene, tetramethylbenzene, pentamethylbenzene, ethylbenzene, n-propylbenzene, isopropylbenzene (cumene), 1-isopropyl-4-methylbenzene (p-cymene), n-butylbenzene, 2-butylbenzene, isobutylbenzene, tert-butylbenzene, n-pentylbenzene, cyclopentylbenzene, neopentylbenzene, cyclohexylbenzene, 1-cyclohexyl-4-methylbenzene, cyclooctylbenzene and the like; or a substituted or unsubstituted polycyclic aromatic hydrocarbon group, e.g., biphenyl, biphenylene, terphenyl, naphthalene, azulene, anthracene, phenanthrene, triphenylene, pyrene, 1-methylnaphthalene, 2-methylnaphthalene, 1-ethylnaphthalene, 2-ethylnaphthalene, 2,21-dimethylbiphenyl, diphenylethane, 1,2-diphenylethane, 1,8-diphenyloctane and the like.

Useful chain transfer moieties include, but are not limited to, dithiocarboxylic ester groups (—S—C(S)R) wherein R is a hydrocarbon group having from 1 to about 20 carbon atoms, including by way of example, straight or branched aliphatic, cycloaliphatic and aromatic groups and cycloaliphatic and aromatic groups substituted with one or more straight or branched aliphatic, cycloaliphatic and/or aromatic groups; trithiocarbamates; benzyl iodides; hydroxyl groups (—OH), ketone groups, alkoxy groups (—OR), carboxyl groups (—COOH), ester groups (—COOR), aldehyde group (—CHO), acyl groups (—C(O)R), amide groups (—C(O)NH₂), substituted amide groups (—C(O)NHR), —C(O)NR₂), amino groups (—NH₂), substituted amino groups (—NHR, —NR₂), nitro groups (—NO₂), nitroso groups (—NO), unsubstituted and substituted cyano groups (—CN), cyanate groups (—OCN), isocyanate groups (—NCO), thiocyanate groups (—SCN), isothiocyanate group (—NCS), thiol group (—SH), and the like.

In another embodiment of the present invention, one $R^2$ is hydrogen and the other $R^2$ is an alkyl of 1 to 6 carbon atoms. In another embodiment, $R^3$ is an alkyl halide group of the formula $(—(R^4)_tCX_3)$ wherein $R^4$ is a hydrocarbon group of 1 to about 12 carbon atoms, t is 0 or 1 and X is a halide, e.g., Cl, F, Br, I with F being preferred. In another embodiment, $R^3$ is the same as $R^1$.

In a preferred embodiment of the present invention, ligand L is a fluorinated. β-diketone having the structure:

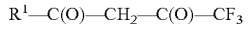

$$R^1—C(O)—CH_2—C(O)—CF_3$$

wherein $R^1$ is a hydrocarbon group having from 1 to about 20 carbon atoms and includes a chain transfer moiety. The chain transfer moiety preferably includes a dithiocarboxylic ester (e.g., RC(S) —S—) functionality wherein R has the aforestated meaning; a trithiocarbonates and/or a benzyl iodide. Preferably, $R^1$ is an aromatic groups such as benzene and/or naphthalene groups.

In general, the complex can be formed by reacting about three moles of ligand (the same ligand or mixed ligands) with about one mole of lanthanide halide such as $EuCl_3$. This reaction is generally carried out in an aqueous solution in the presence of an alkali hydroxide (e.g., NaOH). The ligand is preferably first dissolved in a solvent such as tetrahydrofuran (THF), and the reaction is terminated by the addition of an alcohol (e.g., methanol). The precipitated complex is extracted by filtration with further purification.

Reacting the Lanthanide Complex with the Analyte

The reaction of the lanthanide complex with the target analyte (e.g., an organophosphorus compound) can be carried out by first dissolving the target analyte in a suitable solvent and then reacting it with the complex at a temperature of from ambient to about 100° C. for a sufficient period of time (e.g., about 1 to about 10 hours). If desired, the reaction can be conducted under an inert atmosphere (e.g., in nitrogen, argon, etc.). The resulting adduct can then be separated by known techniques. A preferred target organophosphorus analyte is a compound having the formula $(R^5)(R^6)(R^7)P=O$, wherein $R^5$, $R^6$ and $R^7$ can be the same or different and are individually selected from inorganic or organic groups, provided that at least one group is organic. Exemplary groups include, but are not limited to, those selected from H, —OH, halogen (e.g., F, Cl, Br, I), nitrile (—CN), nitro ($NO_2$), and organic groups such as, for example, substituted or unsubstituted aliphatic or aromatic groups with or without heteroatoms such as, for example, alkyl, cycloalkyl, alkenyl, alkoxy, and the like. The organophosphorus compound is exemplified herein with the use of dimethyl hydrogen phosphate [$(CH_3O)_2P(O)H$], or pinacolyl methyl phosphonate ("PMP") having the formula:

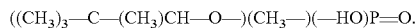

$((CH_3)_3-C-(CH_3)CH-O-)(CH_3-)(-HO)P=O$.

Polymerization

The MIP is prepared by RAFT polymerization of a monomer using the $L_3M$-target analyte adduct.

A wide variety of monomers may be used for synthesizing the MIP in accordance with the principles of the present invention. Suitable non-limiting examples of monomers that can be used for preparing a MIP of the present invention include methylmethacrylate, other alkyl methacrylates, alkylacrylates, allyl or aryl acrylates and methacrylates, cyanoacrylate, styrene, -methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-acryloxy-, '-dimethyl-g-butyrolactone; N-acryloxy succinimide-acryloxytris(hydroxymethyl)aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl) ethyl methacrylate; 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; -bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; -t-butylacrylamide; butyl acrylate; butyl methacrylate; (o,m,p)-bromostyrene; t-butyl acrylate; (R)-carvone; (S)-carvone; (−)-carvyl acetate; c is 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 1-(3-butenyl)-4-vinylbenzene; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstryene; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; (±)-:linalool; linalyl acetate; p-mentha-1,8-diene; p-mentha-6,8-dien-2-ol; methyleneamino acetonitrile; methacrolein; [3-(methacryloylamino)-propyl] trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrite; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; -methyl styrene; t-methylstyrene; t-methylstyrene; 3-methylstyrene; methyl vinyl ether; methyl vinyl ketone; methyl-2-vinyloxirane; 4-methylstyrene; methyl vinyl sulfone; 4-methyl-5-vinylthiazole; myrcene; t-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy)silane; vinyl 2-valerate and the like.

Acrylate-terminated or otherwise unsaturated urethanes, carbonates, and epoxies can also be used in the MIP. An example of an unsaturated carbonate is allyl diglycol carbonate. Unsaturated epoxies include, but are not limited to, glycidyl acrylate, glycidyl methacrylate, allyl glycidyl ether, and 1,2-epoxy-3-allyl propane.

Crosslinking agents that impart rigidity or structural integrity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride and the like.

The polymerization can be carried out neat or in a porogen, or solvent, which can be any solvent suitable for the purposes described herein. Suitable solvents include, but are not limited to, toluene, xylene, methoxyethanol, and the like and mixtures.

Any suitable conditions effective to polymerize the monomers of the present invention to produce an MIP without dissociating the chelated lanthanide-analyte complex may be used. The monomers of the present invention may be polymerized by free radical polymerization, and the like.

Any UV or thermal free radical initiator known to those skilled in the art can be used in the preferred free radical polymerization. Examples of UV and thermal initiators include benzoyl peroxide, acetyl peroxide, lauryl peroxide, azobisisobutyronitrile (AIBN), t-butyl peracetate, cumyl peroxide, t-butyl peroxide; t-butyl hydroperoxide, bis(isopropyl) peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenylacetophenone, and phenothiazine, diisopropylxanthogen disulfide, 2,2'-azobis-(2-amidinopropane); 2,2'-azobisisobutyronitrile-; 4,4'-azobis-(4-cyanovaleric acid); 1,1'-azobis-(cyclohexanecarbonitrile)-; 2,2'-azobis-(2,4-dimethylvaleronitrile); and the like and mixtures thereof.

The choice of monomer and cross-linking agent will be dictated by the chemical (hydrophilicity, chemical stability, degree of cross-linking, ability to graft to other surfaces, interactions with other molecules, etc.) and physical (porosity, morphology, mechanical stability, etc.) properties desired for the polymer. The amounts of chelated lanthanide-analyte complex, monomer and crosslinking agents should be chosen to provide a crosslinked polymer exhibiting the desired structural integrity, porosity and hydrophilicity. The amounts can vary broadly, depending on the specific nature/reactivities of the chelated lanthanide-analyte complex, monomer and crosslinking agent chosen as well as the specific application and environment in which the polymer will ultimately be employed. The relative amounts of each reactant can be varied to achieve desired concentrations of chelated lanthanide-analyte complexes in the polymer support structure. Typically, the amount of chelated lanthanide-analyte complex will be on the order of about 0.01 mmol to about 100 mmol percent of monomer. The solvent, temperature, and means of polymerization can be varied in order to obtain polymeric materials of optimal physical or chemical features, for example, porosity, stability, and hydrophilicity. The solvent will also be chosen based on its ability to solubilize all the various components of the reaction mixture.

Polymerizations are generally conducted in bulk solution by the free-radical method. For bulk polymerization, typically the amount of chelated lanthanide-analyte complex will be on the order of about 0.01 mmol to about 100 mmol percent of monomer, about 90 to about 99 mol percent monomer and about 1.0 to about 10 mol percent cross-linker, and about 1 mol percent of a free radical initiator are dissolved in an aqueous/organic two-phase solvent. The reaction mixture is placed under an inert atmosphere and heated to a temperature of from about 50° C. to about 100° C. for about 24 to about 72 hours. As one skilled in the art will readily appreciate, styrenic polymerizations can be thermally initiated. It is particularly advantageous to prepare a block copolymer employing two or more of the foregoing monomers (See FIG. 2).

When polymerization is complete, the crosslinked polymer may be washed, cryogenically ground to a uniformly fine powder, and/or extensively eluted with nonpolar solvents to remove any unreacted lanthanide-analyte complex. The steps of grinding and/or freezing in liquid nitrogen may be used to maximize surface area and allow for access by the various reagents and samples. Freezing allows the polymer to become brittle enough to be ground and prevents distortions of the polymer by the heat of friction.

Removal of the target molecule leaves a macroporous polymer with complementary molecular cavities which include lanthanide complexes that have specific binding affinity for the target molecule. See FIG. 2. The target molecule comprising, for example, an organophosphorus compound, may be dissociated from the metal ion complex binding site within the polymer in a manner that does not adversely affect the imprinted cavity. In embodiments wherein the target molecule is covalently bound to the functional monomer, any appropriate method can be used to cleave the covalent bond, although the covalent bond formed should preferably be cleaved under conditions suitable to release the imprint molecule after the MIP is formed, without adversely affecting the selective binding characteristics of the MIP. To accomplish this, acetone, isopropanol, methanol or other suitable organic solvent may be used to swell the resultant polymers, allowing greater access to the coordinated metal ions because imprinted resins have a relatively low amount of functionalization and are primarily nonionic matrices. The covalent bond that is cleaved to release the imprint molecule can optionally provide an additional polar or ionic site for design and imprinting of the imprint molecule. In preferred embodiments wherein the target analyte is associated with the lanthanide in a non-covalent manner, the non-covalently bound analyte is simply leached or washed out after polymerization. For example, for organophosphorus compound imprinted resins, subsequent to the removal of unreacted monomer, a 1 N aqueous acidic solution may be mixed into the acetone washes, with increasing aqueous acidic phase in each sequential wash, to remove the imprint molecule from the cavities. In certain preferred embodiments, an acidic solvent having a pH of about 4.5 or less is used. In certain other preferred embodiments, resin mass action is used to replace a target anion with an easily exchangeable anion by immersing the polymer in a solution containing the easily exchangeable anion at a suitable pH.

The polymer of the invention can be prepared in a wide variety of forms ranging from powders to beads to macro structures such as films, plates, rods, membranes or coatings or other materials.

As can be appreciated by the skilled artisan, the preferred synthetic schemes and embodiments described above and in the Examples below are not intended to comprise a comprehensive list of all means by which the polymer described and claimed herein may be synthesized. It will be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described throughout this written description may be performed in an alternate sequence or order to obtain the present invention.

In the following examples, Processable Molecularly Imprinted Polymers (MIPs) were prepared by Reversible Addition Fragmentation Chain Transfer (RAFT) polymerization followed by Ring Closing Metathesis (RCM) to generate the processable MIP. The polymer's core consisted of a dithiobenzoate substituted tri(β-diketonate) europium (III) complex. The β-diketonate was the anion of (dithiobenzoic acid 1-[4-(4,4,4-trifluoro-butane-1,3-dione)-naphthalen-1-yl]-ethyl ester (HDBNTFA). HDBNTFA was prepared by the condensation of dithiobenzoic acid with 4,4,4-trifluoro-1-(4-vinyl-naphthalen-1-yl)-butane-1,3-dione in carbon tetrachloride. The tris DBNTFA europium complex served as a polymerization substrate for three armed RAFT mediated polymers. The arms were AB block copolymers where block A was 1-but-3-phenyl-4-vinylbenzene and block B was styrene. The but-3-phenyls of block A were reacted by RCM with $2^{nd}$ generation Grubb's catalyst to give an intramolecularly crosslinked core. The intramolecularly crosslinked MIP was soluble in common organic solvents and had a molecular weight of approximately 50,000 atomic mass units (amu) and a molecular weight distribution (MWD) of about 1.3.

All reactions and manipulations were carried out under an argon atmosphere using standard Schlenk line techniques. Dry solvents, when needed, were distilled from either Na/benzophenone (aromatics and ethers), or $CaH_2$ (halogenated and nonhalogenated hydrocarbons).

NMR was performed on either a Bruker AC-200 MHz spectrometer or an Anasazi 90 MHz spectrometer; FT-IR was performed on a Bomems MB-122; GC/MS was performed on a Shimadzu QP 5050A. Molecular weight data was determined by a Varian Prostar Model 430 HPLC equipped with a Polymer Laboratories PLgel 5 um MiniMix C, 250×4.6 mm column. The HPLC was calibrated with Polystyrene cal kit S-M-10 and Galaxy Software's GPC Module performed the related calculations.

All chemicals were provided by Sigma-Aldrich or Strem unless otherwise stated, and were used without further purification. Vinyl naphthoyl trifluoroacetone (VNTFA) and 1-but-3-phenyl-4-vinylbenzene were synthesized by previously published methods. Dithiobenzoic acid was synthesized by means found by Rizzardo et al.

Figure 2:
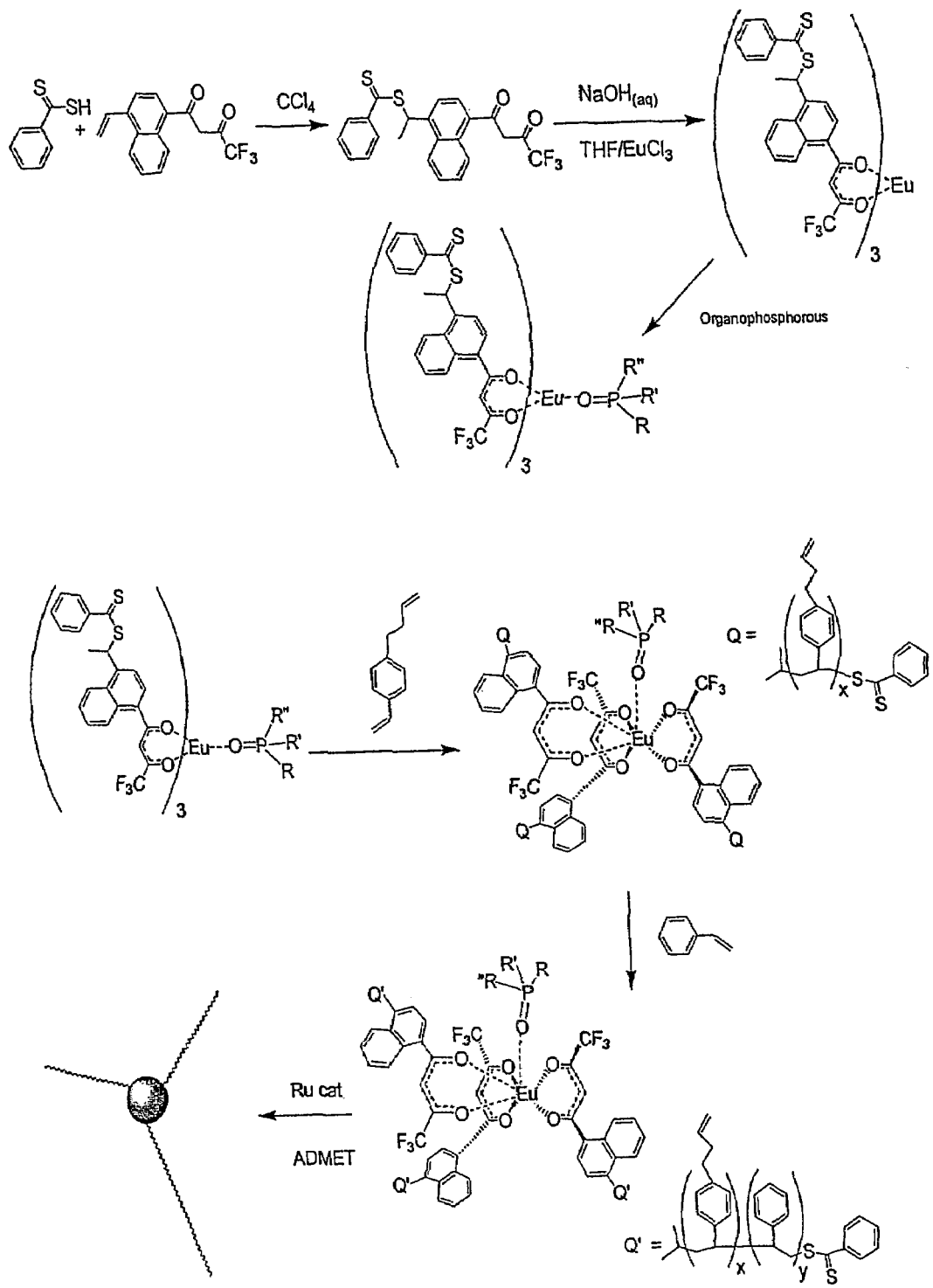

A flow chart of the synthesis procedure as illustrated in Examples 1-5 is presented in FIG. 2.

Example 1

This example illustrates the synthesis of the ligand, (Dithiobenzoic acid 1-[4-(4,4,4-trifluoro-butane-1,3-dione)-naphthalen-1-yl]-ethyl ester (HDBNTFA). Vinyl naphthoyl trifluoroacetone (2.92 g, 10 mmol), dithiobenzoic acid (1.54 g, 10 mmol), and carbon tetrachloride (6 mL) were placed together into a 15 mL roundbottomed flask equipped with a reflux condenser under an argon atmosphere. The reaction was heated to 70° C. for 16 hours when a $2^{nd}$ aliquot of dithiobenzoic acid (0.77 g, 5 mmol) and the reaction was continued for another 4 hours. The solvent was removed by vacuum and the final product was isolated by column chromatography through silica gel with 60/40 hexanes/chloroform as eluent to give a viscous red oil (2.2 g, 50% yield).

Example 2

This example illustrates the synthesis of the europium complex, $(DBNTFA)_3Eu.xH_2O$. HDBNTFA (1.0 g, 2.24 mmol) synthesized in Example 1 was dissolved in THF (5 mL) in a 15 mL roundbottomed flask and 1.0 M sodium hydroxide (2.46 mL) was added dropwise. A solution of europium chloride hexahydrate (0.274 g, 0.75 mmol) in water (2 mL) was added and the flask was equipped with a reflux condenser. The reaction was heated to reflux for 3 hours before excess methanol was added to end the reaction. The precipitate were removed by filtration, dried, dissolved in ether, filtered again, and precipitated into hexanes. The precipitate was isolated by filtration, which gave a red solid (750 mg, 66% yield).

Example 3

This example illustrates the reaction of the europium complex with the target analyte (dimethyl hydrogen phosphate) and a monomer to provide an MIP, i.e., $(DBNTFA)_3Eu.2 (CH_3O)_2P(O)H$-tris(poly-1-but-3-phenyl-4-vinybenzene). $(DBNTFA)_3Eu.xH_2O$ (40 mg, 26 µmol), 1-but-3-phenyl-4-vinylbenzene (880 mg, 5.62 mmol), dimethylhydrogen phosphate (6 mg, 52 µmol), and 2,2'-azobis(2,4-dimethyl valeronitrile) (1.5 mg, 6 µmol) were placed into a reaction flask and the flask was subjected to 3 freeze/pump/thaw cycles. The flask was left under an argon atmosphere and was heated to 50° C. for 7 hours when the excess 1-but-3-phenyl-4-vinylbenzene was removed by vacuum.

Example 4

This example illustrates the preparation of a block copolymer (DBNTFA)$_3$Eu.2(CH$_3$O)$_2$P(O)H-tris(poly-1-but-3-phenyl-4-vinylbenzene-block-polystyrene). Styrene (1.56 g, 15 mmol) was added to the reaction flask from the preceding reaction. The flask was subjected to 3 freeze/pump/thaw cycles, and was heated to 100° C. for 72 hours before the excess styrene was removed by vacuum.

Example 5

This example illustrates the preparation of (DBNTFA)$_3$Eu.2(CH$_3$O)$_2$P(O)H-tris(poly-1-but-3-phenyl-4-vinylbenzene-block-polystyrene)-crosslinked. (DBNTFA)$_3$Eu.2(CH$_3$O)$_2$P(O)H-tris(poly-1-but-3-phenyl-4-vinylbenzene-block polystyrene) (500 mg) and ruthenium catalyst (50 mg, 59 µmol) were placed in at 250 mL Schlenk flask. The flask was evacuated and backfilled 3 times with argon. Methylene chloride (150 mL) was added and the solution was heated to reflux for 18 hours and then room temperature for an additional 6 hours. The solution was filtered through silica gel, the solution concentrated, and the crosslinked polymer precipitated by addition to methanol. A white powder (355 mg) was collected.

Example 6

This example illustrates RAFT polymerization of L$_3$Eu-PMP with methacrylate wherein L is DBNTFA, dithiobenzoic acid 1-[4-(4,4,4-trifluoro-butane-1,3-dione)-naphthalen-1-yl]-ethyl ester.

16 Mmol of ethylene glycol dimethacrylate, 8 mmol methylmethacrylate, 4 mL toluene solvent, 0.44 mmol 2,2'-azobis-(2,4-dimethylvaleronitrile) which is available as Waco V-65 initiator, 0.029 mmol PMP and L$_3$Eu were placed in a disposable glass reaction flash equipped with a stir bar. The solution was subjected to three freeze/pump/thaw cycles with argon backfill. The solution was placed into an oil bath heated to 60° C. for 18 hours before the solvent and unreacted monomer were removed by healing to 60° C. under vacuum (0.5 torr) for 4 hours. The resulting salmon-colored polymer was ground with a freezer mill to a fine powder.

Example 7

Essentially the same procedure as Example 6 was conducted except that the monomers used were 22 mmol divinylbenzene and 11 moles styrene. The resulting salmon-colored powder was ground in a freezer mill to a fine powder.

Example 8

The MIP resulting from Example 6 was cleaned by solvent extraction with isopropanol to remove PMP. The isopropanol was tested for any leached europium and was found to have none, thus showing that the complex is fully incorporated into the polymer and europium does not wash out.

Comparative Example A

An MIP was prepared using mixed ligands 3-vinyldibenzoylmethane and naphthoyltrifluoroacetone complexed with europium using no chain transfer moiety in a matrix of methylmethacrylate and ethylene glycol dimethacrylate. PMP was the target analyte. The polymerization was conducted in accordance with the procedure of Example 6. The resulting MIP was cleaned with isopropanol to remove PMP. However, significant amounts of europium were washed out in the solvent.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A process for preparing a molecularly imprinted polymer for detecting a target analyte comprising the steps of:
   (a) providing a complex comprising a compound of the general formula L$_3$M wherein L is the same or different and is a β-diketone ligand containing the same or different chain transfer moiety and M is a lanthanide element;
   (b) reacting the complex with a target analyte to provide an adduct containing the target analyte;
   (c) co-polymerizing the adduct with a monomer and crosslinking agent to provide a polymer; and,
   (d) removing the target analyte from the polymer to provide the molecularly imprinted polymer.

2. The process of claim 1, wherein the lanthanide element M is europium.

3. The process of claim 1, wherein the ligands L$_3$ are each the same ligand.

4. The process of claim 1, where in two ligands of L$_3$ are the same and the third ligand is different.

5. The process of claim 1, wherein the β-diketone ligands have the structure:

wherein R$^1$ is a hydrocarbon group having 1 to about 20 carbons containing a chain transfer moiety; R$^2$ can be the same or different and is hydrogen or a hydrocarbon group having from 1 to about 12 carbon atoms and R$^3$ is a straight or branched chain alkyl group of 1 to about 12 carbon atoms optionally containing one or more halogen atoms.

6. The process of claim 5, wherein R$^3$ is an alkyl halide.

7. The process of claim 6, wherein the alkyl halide is —CF$_3$.

8. The process of claim 1, wherein the chain transfer moiety is selected from the group consisting of dithiocarboxylic ester, trithiocarbonate and benzyl iodide.

9. The process of claim 8, wherein the dithiocarboxylic ester is of the general formula —S—C(S)R wherein R is a hydrocarbon group having from 1 to about 20 carbon.

10. The process of claim 1, wherein the analyte is an organophosphorus compound.

11. The process of claim 10, wherein the organophosphorus compound has the formula (R$^5$)(R$^6$)(R$^7$)P═O, wherein R$^5$, R$^6$ and R$^7$ can be the same or different and are individually selected from inorganic or organic groups, provided that at least one group is organic.

12. The process of claim 11, wherein the inorganic groups are selected from the group consisting of H, —OH, F, Cl, Br, I, —CN and —NO$_2$, and the organic groups are substituted or unsubstituted aliphatic or aromatic groups with or without heteroatoms.

13. The process of claim 10, wherein the organophosphorus compound is selected from the group consisting of dimethyl hydrogen phosphate and pinacolyl methyl phosphonate.

14. The process of claim 1, wherein each ligand L is a fluorinated β-diketone having the structure:

$$R^1-C(O)-CH_2-C(O)-CF_3$$

wherein $R^1$ is a hydrocarbon group which includes as the chain transfer moiety a moiety selected from the group consisting of dithiocarboxylic ester, trithiocarbonate and benzyl iodide.

15. The process of claim 1, wherein the crosslinking agent is selected from the group consisting of difunctional acrylates, difunctional methacrylates, trifunctional acrylates, trifunctional methacrylates, tetrafunctional acrylates, tetrafunctional methacrylates, divinylbenzene, alkylene glycol diacrylates, alkylene glycol methacrylates, polyalkylene glycol diacrylates, polyalkylane glycol methacrylates, vinyl acrylates, vinyl methacrylates, allyl acrylates, allyl methacrylates, divinylbenzene, diallyldiglycol dicarbonate, diallyl maleate, diallyl fumarate, diallyl itaconate, divinyl oxalate, divinyl malonate, diallyl succinate, triallyl isocyanurate, bisphenol A dimethacrylate, bis-phenol A diacrylate, ethoxylated bis-phenol A dimethacrylate, ethoxylated bis-phenol A diacrylate, methylene bisacrylamide, methylene bismethylacrylamide, polymethylene bisacrylamide, polymethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methyl-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride and mixtures.

16. The process of claim 1, wherein the co-polymerization step (c) is performed in the presence of an initiator.

17. The process of claim 16, wherein the initiator is selected from the group consisting of benzoyl peroxide, acetyl peroxide, lauryl peroxide, azobisisobutyronitrile, t-butyl peracetate, cumyl peroxide, t-butyl peroxide; t-butyl hydroperoxide, bis(isopropyl)peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenylacetophenone, phenothiazine, diisopropylxanthogen disulfide, 2,2'-azobis-(2-amidinopropane), 4,4'-azobis-(4-cyanovaleric acid), 1,1'-azobis-(cyclohexanecarbonitrile)-, and mixtures thereof.

18. The process of claim 1, wherein the step of removing the target analyte comprises washing the polymer with a solution capable of leaching the analyte.

19. The process of claim 18, wherein the leaching solution includes a compound selected from the group consisting of acetone, isopropanol, methanol, N,N-dimethylformamide, dimethyl sulfoxide, N-methylpyrrolidinone, and mixtures thereof.

20. The process of claim 1, wherein the copolymerization step (c) is performed neat or in a solvent.

21. The process of claim 1, wherein the monomer is selected from the group consisting of acrylic acid, methacrylic acid, alkyl methacrylates, alkyl acrylates, allyl acrylates, allyl methacrylates, aryl acrylates, aryl methacrylates, cyanoacrylate, styrene, -methyl styrene, vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-acrylox, '-dimethyl-g-butyrolactone; N-acryloxy succinimide-acryloxytris(hydroxymethyl)aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl) acrylic acid; 8-bromo-1-octene; 5-bromo-1-pentene; cis-1-bromo-1-propene;.-bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; -t-butylacrylamide; butyl acrylate; butyl methacrylate; (o,m,p)-bromostyrene; t-butyl acrylate; (R)-carvone; (S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstryene; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether, ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; (±)-:linalool; linalyl acetate; p-mentha-1,8-diene; p-mentha-6,8-dien-2-ol; methyleneamino acetonitrile; methacrolein; [3-(methacryloylamino)-propyl] trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrite; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; -methyl styrene; t-methylstyrene; t-methylstyrene; 3-methylstyrene; methyl vinyl ether; methyl vinyl ketone; methyl-2-vinyloxirane; 4-methylstyrene; methyl vinyl sulfone; 4-methyl-5-vinylthiazole; myrcene; t-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy) silane, vinyl 2-valerate, 1-(3-butenyl)-4-vinylbenzene and mixtures thereof.

22. The process of claim 1, wherein the polymer is a block copolymer.

23. A polymer comprising the reaction product of (a) a complex comprising a compound of the general formula $L_3M$ wherein L is the same or different and is a β-diketone ligand containing the same or different chain transfer moiety and M is a lanthanide element, the complex being capable of binding an analyte to be detected; (b) a monomer; and (c) optional crosslinking agent, wherein said polymer undergoes a detectable luminescence change upon exposure to the analyte to be detected.

24. The polymer of claim 23, wherein the β-diketone ligands have the structure:

$$R^1-C(O)-CR^2_2-C(O)-R^3$$

wherein $R^1$ is a hydrocarbon group having 1 to about 20 carbons containing a chain transfer moiety; $R^2$ can be the same or different and is hydrogen or a hydrocarbon group having from 1 to about 12 carbon atoms and $R^3$ is a straight or branched chain alkyl group of 1 to about 12 carbon atoms optionally containing one or more halogen atoms.

25. The polymer of claim 24, wherein $R^3$ is an alkyl halide.

26. The polymer of claim 25, wherein the alkyl halide is $-CF_3$.

27. The polymer of claim 23, wherein the chain transfer moiety is selected from the group consisting of dithiocarboxylic ester, trithiocarbonate and benzyl iodide.

28. The polymer of claim 23, wherein the lanthanide element M is europium and the chain transfer moiety is a dithiocarboxylic ester of the general formula $-S-C(S)R$ wherein R is a hydrocarbon group having from 1 to about 20 carbon.

29. The polymer of claim 23, wherein the analyte is an organophosphorus compound.

30. The polymer of claim 29, wherein the organophosphorus compound is selected from the group consisting of dimethyl hydrogen phosphate and pinacolyl methyl phosphonate.

31. The polymer of claim 23, wherein each ligand L is a fluorinated β-diketone having the structure:

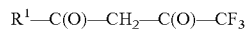

$$R^1-C(O)-CH_2-C(O)-CF_3$$

wherein $R^1$ is a hydrocarbon group which includes as the chain transfer moiety a dithiocarboxylic ester and the lanthanide element M is europium.

32. The polymer of claim 23, wherein monomer is selected from the group consisting of acrylic acid, methacrylic acid, alkyl methacrylates, alkyl acrylates, allyl acrylates, allyl methacrylates, aryl acrylates, aryl methacrylates, cyanoacrylate, styrene, -methyl styrene, vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-acryloxy, '-dimethyl-g-butyrolactone; N-acryloxy succinimide-acryloxytris(hydroxymethyl)aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl) acrylic acid; 8-bromo-1-octene; 5-bromo-1-pentene; cis-1-bromo-1-propene; -bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; -t-butylacrylamide; butyl acrylate; butyl methacrylate; (o,m,p)-bromostyrene; t-butyl acrylate; (R)-carvone;

(S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstryene; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; (±)-:linalool; linalyl acetate; p-mentha-1,8-diene; p-mentha-6,8-dien-2-ol; methyleneamino acetonitrile; methacrolein; [3-(methacryloylamino)-propyl] trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl) trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; -methyl styrene; t-methylstyrene; t-methylstyrene; 3-methylstyrene; methyl vinyl ether; methyl vinyl ketone; methyl-2-vinyloxirane; 4-methylstyrene; methyl vinyl sulfone; 4-methyl-5-vinyithiazole; myrcene; t-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidazole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy) silane, vinyl 2-valerate, 1-(3-butenyl)-4-vinylbenzene and mixtures thereof.

33. The polymer of claim 23, wherein the polymer is a block copolymer.

34. A molecularly imprinted polymer obtained by the steps of (a) providing a reaction product of(i) a complex comprising a compound of the general formula $L_3M$ wherein L is the same or different and is a β-diketone ligand containing the same or different chain transfer moiety and M is a lanthanide element and (ii) a target analyte; (b) copolymerizing the reaction product of step (a) with monomer and optional crosslinking agent to form a polymer; and (c) removing the target analyte from the polymer to provide a molecularly imprinted polymer which selectively binds to the target analyte and undergoes a detectable luminescence change when the target analyte binds thereto.

35. The molecularly imprinted polymer of claim 34, wherein the ligands $L_3$ are each the same ligand.

36. The molecularly imprinted polymer of claim 34, wherein the β-diketone ligands have the structure:

$$R^1-C(O)-CR^2_2-C(O)-R^3$$

wherein $R^1$ is a hydrocarbon group having 1 to about 20 carbons containing a chain transfer moiety; $R^2$ can be the same or different and is hydrogen or a hydrocarbon group having from 1 to about 12 carbon atoms and $R^3$ is a straight or branched chain alkyl group of 1 to about 12 carbon atoms optionally containing one or more halogen atoms.

37. The molecularly imprinted polymer of claim 36, wherein $R^3$ is an alkyl halide.

38. The molecularly imprinted polymer of claim 37, wherein the alkyl halide is —$CF_3$.

39. The molecularly imprinted polymer of claim 34, wherein the chain transfer moiety is selected from the group consisting of dithiocarboxylic ester, trithiocarbonate and benzyl iodide.

40. The molecularly imprinted polymer of claim 34, wherein the lanthanide element M is europium and the chain transfer moiety is a dithiocarboxylic ester of the general formula —S—C(S)R wherein R is a hydrocarbon group having from 1 to about 20 carbon.

41. The molecularly imprinted polymer of claim 34, wherein the analyte is an organophosphorus compound.

42. The molecularly imprinted polymer of claim 41, wherein the organophosphorus compound is selected from the group consisting of dimethyl hydrogen phosphate and pinacolyl methyl phosphonate.

43. The molecularly imprinted polymer of claim 34, wherein each ligand L is a fluorinated β-diketone having the structure:

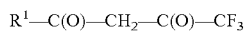

wherein $R^1$ is a hydrocarbon group which includes as the chain transfer moiety a moiety selected from the group consisting of dithiocarboxylic ester, trithiocarbonate and benzyl iodide and the lanthanide element M is europium.

44. The molecularly imprinted polymer of claim 34, wherein monomer is selected from the group consisting of acrylic acid, methacrylic acid, alkyl methacrylates, alkyl acrylates, allyl acrylates, allyl methacrylates, aryl acrylates, aryl methacrylates, cyanoacrylate, styrene, -methyl styrene, vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy) ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-acryloxy, '-dimethyl-g-butyrolactone; N-acryloxy succinimide acryloxytris(hydroxymethyl)aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl) ethyl methacrylate; 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; -bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; -t-butylacrylamide; butyl acrylate; butyl methacrylate; (o,m,p)-bromostyrene; t-butyl acrylate; (R)-carvone; (S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstryene; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1, 6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; (±)-:linalool; linalyl acetate; p-mentha-1,8-diene; p-mentha-6,8-dien-2-ol; methyleneamino acetonitrile; methacrolein; [3-(methacryloylamino)-propyl] trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl) trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrite; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; -methyl styrene; t-methylstyrene; t-methylstyrene; 3-methylstyrene; methyl vinyl ether; methyl vinyl ketone; methyl-2-vinyloxirane; 4-methylstyrene; methyl vinyl sulfone; 4-methyl-5-vinylthiazole; myrcene; t-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2, 4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotonoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy) silane, vinyl 2-valerate, 1-(3-butenyl)-4-vinylbenzene and mixtures thereof.

45. The molecularly imprinted polymer of claim 34, wherein the polymer is a block copolymer.

* * * * *